United States Patent [19]

Marcin

[11] Patent Number: 5,073,707

[45] Date of Patent: Dec. 17, 1991

[54] WINDOW-TRANSMITTANCE METER HAVING ENTRANCE DETECTOR

[75] Inventor: Edward Marcin, Scituate, Mass.

[73] Assignee: Laser Labs, Inc., Scituate, Mass.

[21] Appl. No.: 528,750

[22] Filed: May 24, 1990

[51] Int. Cl.$^5$ .............................................. G01N 9/04
[52] U.S. Cl. ................................ 250/223 R; 356/239
[58] Field of Search .................. 250/223 R, 571, 572, 250/569; 356/239, 432–434, 394; 209/586

[56] References Cited

U.S. PATENT DOCUMENTS

| | | | |
|---|---|---|---|
| 3,765,778 | 10/1973 | Bey et al. | 356/434 |
| 3,956,632 | 5/1976 | Hall et al. | 250/223 R |
| 4,043,676 | 8/1977 | Holzinger et al. | 356/226 |
| 4,076,425 | 2/1978 | Saltz | 250/575 |
| 4,107,539 | 8/1978 | Kirsch | 250/223 R |
| 4,124,301 | 11/1978 | Pocock | 250/573 |
| 4,268,746 | 5/1981 | Schroeder | 250/223 R |
| 4,365,718 | 12/1982 | Howerton | 250/223 R |
| 4,558,216 | 12/1985 | Rodi et al. | 250/223 R |
| 4,685,982 | 8/1987 | Kucheck | 250/223 R |

*Primary Examiner*—David C. Nelms
*Assistant Examiner*—Stephone Allen
*Attorney, Agent, or Firm*—Cesari & McKenna

[57] ABSTRACT

A light-transmittance meter (10) employs a housing (12) that forms a slot (16) in which the edge of a window pane (14) can be received. A microswitch (24) detects initial insertion of the window (14) into the slot (16) and causes a sample-and-hold circuit (32) to store a value representing the output that a photodiode (20) produces in response to light received from a light-emitting diode 18 before the window pane (14) is interposed between them. A ratio meter (36) then receives the output of the photodiode (20) when the window (14) has been interposed between the LED (18) and the photodiode (20), and it generates a display (22) of the ratio of that value to the initial, reference value determined before the window 14 was completely inserted.

5 Claims, 2 Drawing Sheets

WINDOW-TRANSMITTANCE METER HAVING ENTRANCE DETECTOR

BACKGROUND OF THE INVENTION

The present invention is directed to measurement of light transmittance. It finds particular, although not exclusive, application to the transmittance of automobile window glass.

The tinting of automobile window glass has become subject to regulation in some jurisdictions. Large numbers of personnel in the law-enforcement, inspection, and installation communities must therefore be employed to measure window-glass light transmittance. Because of the large number of personnel involved, it is important that no great degree of training be required to enable the personnel to make the necessary measurements.

It is accordingly an object of the present invention to permit such measurements to be made reliably and accurately by personnel who have little or no training.

SUMMARY OF THE INVENTION

The foregoing and related objects are achieved in an apparatus that includes a light source and detector mounted in a housing that forms a slot into which a window pane can be inserted. The source and detector are so disposed with respect to each other that there is a free-air path between the source and detector before a glass pane is inserted. Insertion of a glass pane all the way into the receptacle interposes the pane between the source and detector. A position sensor, typically in the form of a microswitch, senses the initial entrance of a glass pane into the receptacle before the pane has been inserted far enough to intersect the light path. The resultant output of the position detector causes comparison circuitry to store the light-detector output's initial value, i.e., a value that represents the transmittance of the air. The comparison circuit then uses that initial value as a reference in generating an output representative of the value that the light-detector output assumes later, when the glass has been completely inserted. Specifically, the comparison-circuit output represents the ratio between the later output and the reference output. It thus provides an indication of the window's transmittance.

The apparatus can thus be arranged to operate without any action on the part of the user except his insertion of the pane into the receptacle. Moreover, because the apparatus uses the same source and detector to make the glass-transmittance measurement that it used to make the reference measurement typically less than a minute before, it avoids almost all of the inaccuracies that result from aging and circuit drift.

The invention is typically embodied in a battery-operated device. If the position detector additionally is interposed electrically between the battery and the other circuitry, operating personnel do not even have to turn the meter on or off.

The invention thus provides an easy and effective way to implement light-transmittance regulations without any significant investment in personnel training.

BRIEF DESCRIPTION OF THE DRAWINGS

These and further features and advantages of the present invention are described in connection with the accompanying drawings, in which.

DETAILED DESCRIPTION OF AN ILLUSTRATIVE EMBODIMENT

Figure 1:
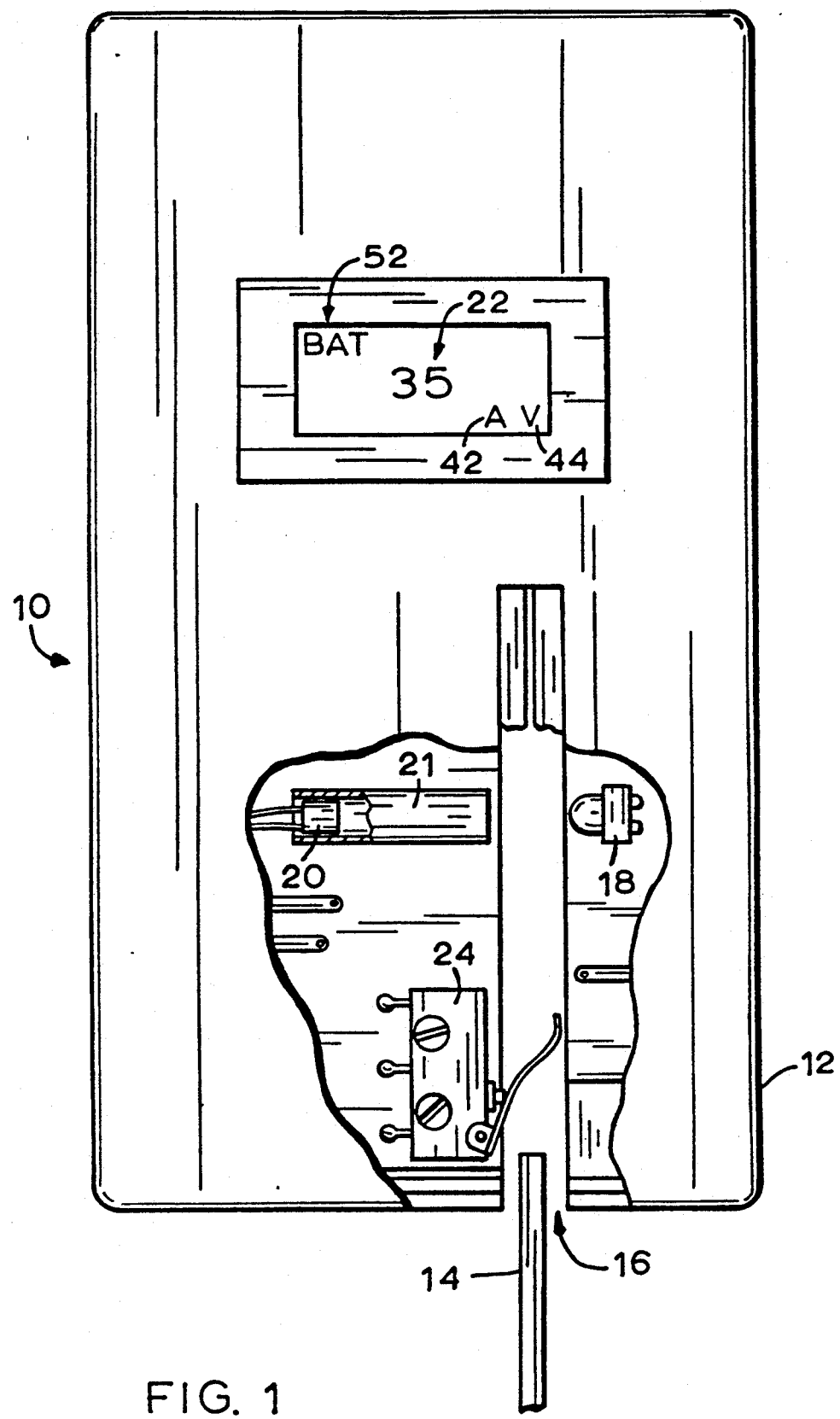
FIG. 1 is a front elevation, with parts broken away, of a meter that employs the teachings of the present invention.

To operate a light-transmittance meter 10 depicted in FIG. 1, a user places its housing 12 over a window 14 in such a manner that the edge of the window 14 enters a receptacle or slot 16 formed by the housing 12. FIG. 1 shows the meter 10 with the edge of the window pane 14 only beginning to be inserted into the slot. To make the measurement, however, the user inserts the window 14 all the way into the slot 16 so that the window is interposed in the light path between a light source 18 and a light detector 20. The light source 18 is a light-emitting diode (LED), and the light detector 20 is a photodiode disposed at the end of a narrow tube 21, which permits light from the LED 18 to reach the photodiode 20 but tends to prevent light from other sources from reaching it. When the window has been completely inserted, the user simply reads the transmittance percentage from an LCD display 22.

As the window is initially inserted it engages a position detector in the form of a microswitch 24, which connects an internal battery to the source 18, the detector 20, and all of the other internal circuitry to enable it to operate. When the user has finished taking a reading, he simply removes the meter, and the microswitch 24 returns to its open state and disconnects the battery. The user thus needs to take no separate action even to turn the device on or off.

Figure 2:
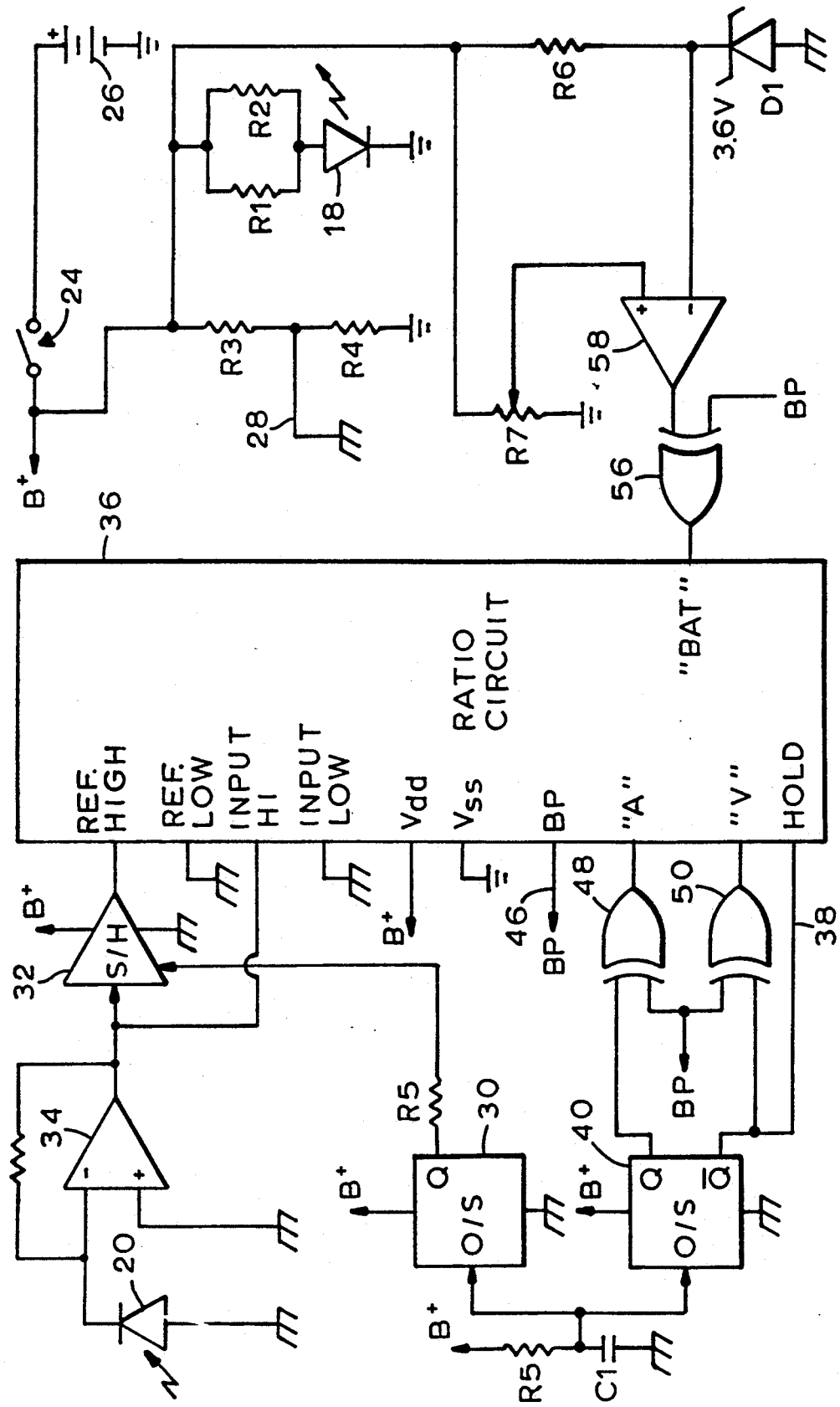
FIG. 2 is a schematic diagram that depicts the circuitry that the meter employs.

FIG. 2 depicts circuitry for implementing these functions. When the microswitch 24 closes, it connects the positive terminal of a battery 26 to the B+ supply rail from which the LED 18, the photodiode 20, and the comparison circuitry depicted in the remainder of FIG. 3 ultimately receive power. Power is thereby applied through resistors R1 and R2 to the light-emitting diode 18. Closure of the microswitch 24 also connects the battery 26 to a voltage divider comprising resistors R3 and R4, which provides a reference potential on node 28 that serves as the ground potential for most of the circuitry. The potential of this "second" ground is higher than that of the "first" ground at the negative terminal of the battery 26.

The output of the microswitch 24, i.e., the positive-rail voltage B+, is applied to a bounce filter comprising a resistor R5 and a capacitor C1. The resultant output has a rise time of approximately 12 μsec. and triggers a 68-μsec. one-shot 30. When one-shot 30 times out, it triggers a sample-and-hold circuit 32, causing it to sample the output of an amplifier 34. The amplifier output is an amplified version of the output of the photodiode 20, so the sample-and-hold output represents the light intensity that the photodiode 20 received approximately 80 μsec. after the switch closed. Since 80 μsec. is not enough time for the window to have been inserted all the way into the slot, the sample-and-hold output represents the light that results from 100% transmittance, i.e., from the transmittance of the air in the path between the LED 18 and the photodiode 20. A ratio-indicating panel meter 36, such as the VK1000H meter available from Digimeter, Inc., of Milpitas, Calif., receives the sample-and-hold output as its reference input, i.e., as the denominator of the ratio that the panel meter is to compute. The numerator is the output of the amplifier 34; that is, the numerator represents the current light intensity. The meter presents the computed ratio on the LCD display 22 and thereby provides an indication of the glass transmittance.

Although this completes the transmittance measurement, the particular panel meter 36 employed in the illustrated embodiment includes a hold feature, which freezes the panel-meter reading in response to a high-going signal on line 38. To take advantage of this feature, the illustrated embodiment employs a second, three-second one-shot 40. Like the first one-shot 30, the second one-shot 40 is triggered by the filtered output of the microswitch 24 that occurs when the pane 14 first enters the slot 16.

When one-shot 40 times out, its Q output, which appears on line 38, goes high and thereby causes the panel meter 36 to hold the reading that it was displaying at that time. The three-second duration of the one-shot-40 output pulse gives the user plenty of time to insert the window 14 all the way into the slot, so the held meter output represents the glass transmittance.

To indicate whether the panel meter 36 has yet frozen its reading, it provides two alternately illuminable segments 42 and 44 in the shapes of an A for "acquisition" and a V for "valid," respectively. Controlling these segments involves the use of a panel-meter output BP on line 46, which is the square-wave voltage that the meter applies to the common LCD electrode. Each of two XOR gates 48 and 50 receives this square-wave signal as one input. As its other input, gate 48 receives the Q output of the three-second one-shot 40, while gate 50 receives the Q̄ output. The output of gate 48 is thus 180° out of phase with the common-electrode signal BP so long as the Q output of one-shot 40 is high, i.e., so long as one-shot 40 is in its unstable state. Gate 48 applies this output to the A segment electrode, so an AC voltage appears across the A segment and causes an A to appear on the display. At the same time, the output of XOR gate 50, which receives the Q̄ output of one-shot 40, is in phase with BP, so no potential difference appears across the V segment. The V segment is accordingly invisible.

After one-shot 40 times out, on the other hand, the signals that it applies to the XOR gates are reversed. The A therefore disappears, and the V appears on the display to tell the user that the reading has now been frozen and he can record it at his leisure.

The illustrated embodiment additionally includes a low-battery indicator comprising an LCD segment that displays the letters "BAT" (battery) to which numeral 52 refers in FIG. 1. Like the A and V segments, the BAT segment receives the square-wave BP signal at its common electrode. At its segment electrode, it receives the output of an XOR gate 56, which receives the BP signal as one of its inputs. The other gate-58 input is the output of a comparator 58, which determines whether the battery voltage is high enough.

Specifically, the comparator 58 compares the output of a potentiometer R7 with the voltage at one terminal of a zener diode D1. Diode D1 is connected between the second ground and a resistor R6 connected to the positive electrode of the battery 26, while the potentiometer R7 is connected across the battery 26. If the battery voltage is the intended 9 volts, the output of the potentiometer R7 is lower than the voltage at the upper end of zener diode D1, so the comparator output is low. The output of gate 56 is accordingly in phase with the BP signal, so the BAT display is not visible.

When the battery voltage falls too far below the 9-volt level, however, the potentiometer output becomes higher than the potential at the upper terminal of the zener diode D1. The comparator output therefore goes high, and the resultant out-of-phase output of XOR gate 56 causes the BAT display to become visible.

From the foregoing discussion, it is apparent that a meter employing the teachings of the present invention can readily be used by personnel who have little or no training. Moreover, it ordinarily requires no maintenance except for the occasional replacement of a battery. It thus permits transmittance regulations to be implemented without any significant investment in training.

I claim:
1. For testing the transmittance of window glass, an apparatus comprising:
   A) a housing forming a receptacle adapted for insertion of a glass pane thereinto;
   B) a light source for emitting light and a light detector for receiving light and generating a light-detector output indicative of the intensity of the received light, the light source and detector being so mounted in the housing with respect to each other and the receptacle that the light source shines light through a glass pane to the light detector when the pane is completely inserted into the receptacle but shines light directly to the detector when the pane is in a entrance range of positions of partial insertion;
   C) a position detector for detecting the entry of a pane into a position within the entrance range and generating a presence indication in response; and
   D) a comparison circuit responsive to the presence indication and the light-detector output for storing a reference value representing the value that the light-detector output assumes at a point in time determined by the time at which the position indicator initially generates the presence indication and for generating an output indicative of the ratio that the intensity represented by the light-detector output at a subsequent time bears to the intensity represented by the reference value.

2. An apparatus as defined in claim 1 wherein the position detector includes a mechanical switch that includes an operating element movable between open and closed positions, in which the switch assumes its open and closed states, respectively, the operating element being so disposed in the receptacle as to be moved from one of its positions to the other by the passage of a glass pane through the entrance range of positions.

3. An apparatus as defined in claim 1 including:
   A) a power source connected to supply power to the light source, the light detector, and at least part of the comparison circuitry;
   B) a switch responsive to the absence of a glass pane from the receptacle to maintain its open state and responsive to passage of a glass pane through a position in the entrance range to assume its closed state, the switch being electrically interposed in the connection between the power source and at least one of the light source, the light detector, and at least part of the comparison circuitry.

4. An apparatus as defined in claim 3 wherein the position detector comprises the switch.

5. An apparatus as defined in claim 4 wherein the switch is a mechanical switch that includes an operating element movable between open and closed positions, in which the switch assumes its open and closed states, respectively, and is so disposed in the receptacle as to be moved from one of its positions to the other by the passage of a glass pane through the entrance range of positions.

* * * * *